United States Patent [19]
Virtanen et al.

[11] Patent Number: 5,773,052
[45] Date of Patent: Jun. 30, 1998

[54] BETAINE AS A SUBSTITUTE FOR SUPPLEMENTARY METHIONINE IN ANIMAL DIETS

[75] Inventors: Erkki Virtanen; Mika Koivistoinen, both of Helsinki, Finland; David D. Hall, Quincy, Ill.; James L. McNaughton, Easton, Md.

[73] Assignee: Cultor-Ltd, Helsinki, Finland

[21] Appl. No.: 426,016

[22] Filed: Apr. 20, 1995

Related U.S. Application Data

[63] Continuation of Ser. No. 53,138, Apr. 29, 1993, abandoned.

[51] Int. Cl.$^6$ ............................................. A01K 1/00
[52] U.S. Cl. ........................... 426/2; 424/442; 426/231; 426/442; 426/623; 426/635; 426/648; 426/807
[58] Field of Search .............................. 426/2, 231, 442, 426/623, 635, 648, 807; 424/442

[56] References Cited

U.S. PATENT DOCUMENTS

| | | | |
|---|---|---|---|
| 3,959,519 | 5/1976 | Johnson | 426/648 |
| 4,218,438 | 8/1980 | Callender et al. | |
| 4,857,555 | 8/1989 | Smith et al. | |
| 5,063,219 | 11/1991 | Schildknecht et al. | |
| 5,314,700 | 5/1994 | Barnes et al. | |
| 5,397,803 | 3/1995 | Smith et al. | |

FOREIGN PATENT DOCUMENTS 291705  1/1971  U.S.S.R. ................................ 426/807

OTHER PUBLICATIONS

McNaughton, J.L., "Biological Availability of Betaine for the Placement of Methionine for Growing Broiler Chickens" (Jun. 30, 1992).

Baker, D.H. and Czarnecki, G.L., "Transmethylation of Homocysteine to Methionine: Efficiency in the Rat and Chick," *J. Nutr.* 115:1291–1299 (1985).

McGinnis, J. et al., "Effect of Ethanolamine and Betaine on Perosis in Chicks," *Proc. Soc. Exp. Biol. Med.* 51(2):293–294 (1942).

McNaughton, J. L., "Effect of Betaine on the Potentiation of an Ionophore Coccidiostat (Bio–Cox) in the Control of Coccidiosis for Growing Broiler Chickens", *Summary Report by Finnsugar Bioproducts*, Letter and Data sent to distributors in Mar., 1993. 8 pages.

Nutrient Requirements of Poultry, National Research Council, 9:27–28 (1994).

Saunderson, C.L. et al., Changes in Body–weight, Composition and Hepatic Enzyme Activities in Response to Dietary Methionine, Betaine and Choline Levels in Growing Chicks, British Journal of Nutrition, 63:339–349 (1990).

Tsiagbe, V.K. et al., Enhanced Immune Responses in Broiler Chicks Fed Methionine–Supplemental Diets, Poultry Science, 66:1147–1154 (1987).

Baker, D.H., Amino Acid Interactions with Vitamins, Minerals and Drugs, NFIA pp. 1–9 (1984).

Hafez et al., Methionine Toxicity in Chicks and Poults, *Poultry Science* 57:699–703 (1978).

Harter et al., Factors Affecting Methionine Toxicity and Its Alleviation in the Chick, *J. Nutr.* 108:1061–1070 (1978).

Pesti et al., Sulfur Amino Acid and Methyl Donor Status of Corn–Soy Diets, *Poultry Science* 58:1541–1547 (1979).

H. Patrick et al., *Poultry: Feeds & Nutrition,* Second Edition, AVI Publishing Co. Inc., Westport, Conn., Chapters 36–38 (1980).

M. Scott et al., *Nutrition of the Chicken,* Second Edition, M.L. Scott & Associates, Ithaca, N.Y., pp. 104 and 469 (1976).

H. Titus et al., *The Scientific Feeding of Chickens,* Fifth Edition, The Interstate Publishers, Danville, IL pp. 230–233 and Chapter 13, pp. 245–311 (1971).

*Primary Examiner*—John J. Gallagher
*Attorney, Agent, or Firm*—Sterne, Kessler, Goldstein, & Fox P.L.L.C.

[57] ABSTRACT

This invention is directed to diets for chicks designed to provide their dietary requirements of methionine. Betaine is used in place of methionine to supply a portion of this requirement.

27 Claims, 7 Drawing Sheets

BETAINE AS A SUBSTITUTE FOR SUPPLEMENTARY METHIONINE IN ANIMAL DIETS

This application is a continuation of application Ser. No. 08/053,138, filed Apr. 29, 1993, now abandoned.

TECHNICAL FIELD

This invention relates to industrial diets for chicks, which are balanced to meet the amino acid requirements of the animals by adding nutritional supplements.

BACKGROUND OF THE INVENTION

Many of the plant feedstuffs commonly used as raw materials for industrial poultry diets are too low in methionine to meet the nutritional requirements of the animals. The deficiency is seen as retarded growth, lowered feed conversion efficiency and increased body fat. In order to correct for this deficiency, the diets in commercial use are normally supplemented with synthetic methionine. The methionine addition to practical broiler diets used in the USA accounts for 1–2.5 kg/tn in starter diets (fed from 1 to 21 days of the chick's age), 0.5–1.5 kg/tn in grower diets (21–40 days of age) and 0.5–1 kg/tn in a finisher diets (40–49 days of age). The supplemental methionine typically accounts for 10–50% of the total methionine requirement of chicks.

Betaine has been studied experimentally for its ability to replace methionine. An ability to substitute may result from either of two related biological properties. First, as an effective methyl donor, betaine may replace methionine in transmethylation reactions (Stekol et al., *J. Biol. Chem.* 203:763–773 (1953)). Second, betaine can transfer methyl groups to homocysteine to produce methionine itself (Harper, in *Review of Physiol. Chem.*, 120 and 351 (1973)). Nevertheless, dietary methionine and dietary betaine are not equivalent in all respects. For example, the addition of moderate levels (e.g. 0.5%) of methionine to a basal diet containing 0.37% methionine has been reported to be toxic to chicks whereas the equivalent addition of betaine is not toxic (Harter et al., *J. Nutr.* 108:1061–1070 (1978); Hafez et al., *Poultry Sci.* 57:699–703 (1978)).

Methionine is a versatile nutrient known to have several distinct biological functions. Specifically, methionine may donate sulfur groups, methyl groups or serve as a building block of proteins. The diverse biological functions performed by methionine may be reflected in diverse dietary requirements. For example, a chick may require a certain percentage of dietary methionine for protein synthesis which is different from its need for methionine as a donor in transmethylation reactions. This suggests that a molecule such as betaine may replace methionine for certain purposes but not others and that a combination of methionine and betaine may be more effective than methionine alone. However, early studies failed to support this proposition. For example, Pesti et al. found that there was no significant difference in chick growth or feed conversion efficiency when a diet containing 0.37% methionine was supplemented with 0.23% betaine in place of 0.23% added methionine (*Poultry Science* 58:1541–1547, 1546 (1979)). Perhaps because of this and similar studies, the broiler industry presently uses methionine levels of about 0.52% and 0.46% in starter and grower diets respectively and typically does not supplement with betaine at all (see e.g., H. Titus et aL, *The Scientific Feeding of Chickens*, Fifth Edition, The Interstate Publishers, Danville, Ill. pp. 230–232 (1971); M. Scott et al., *Nutrition of the Chicken*, Second Edition, M. L. Scott & Associates, Ithaca, N.Y., pp. 104 and 469 (1976)).

The inventors reinvestigated the replacement of methionine with betaine. They found that at high levels of methionine (0.60%), added betaine and methionine worked equally well. However, when starter and grower diets were brought to initial methionine concentrations of 0.37% and 0.31% respectively, the addition of 0.15% betaine was significantly more effective than methionine at reducing chick mortality and improving feed conversion efficiency. The addition of betaine also resulted in chicks with significantly improved carcass quality in terms of reduced body fat. Thus, when studies similar to those of Pesti were repeated with supplementation levels more typical of those used in industry, (0.15% methionine or betaine giving a total combined concentration of 0.52% for starter diets and 0.46% for grower diets, rather than 0.23% methionine or betaine giving a total combined concentration of 0.60%), entirely different and unexpected results were obtained (for examples of methionine levels in typical formulations used in the industry, see H. Titus et al., *The Scientific Feeding of Chickens*, Fifth Edition, The Interstate Publishers, Danville, Ill. pp. 230–232 (1971); see also H. Patrick et al., *Poultry: Feeds & Nutrition*, Second Edition, AVI Publishing Co. Inc., Westport, Conn., pp. 442–443 (1980)). Based upon these results, the inventors have developed a new method for supplementing the diets of chicks.

SUMMARY OF THE INVENTION

The present invention is directed to a method of providing the dietary requirements of chicks by supplementing basal diets with betaine. Provided that a minimum methionine level of 0.37% in starter diets and 0.31% in grower and finisher diets is reached with raw feedstuffs and supplemental methionine, further supplementation in the range of between 0.01% and 0.4% is made more efficiently with betaine than methionine. Preferably, between 0.05% and 0.2% betaine is added to starter, grower and finisher diets and more preferably 0.15% is added. Supplementation with betaine results in a higher response than an equivalent amount of methionine in terms of the growth, feed efficiency and carcass quality of broilers.

The present invention is also directed to diets for chicks comprised of a basal diet formulated with standard feedstuffs, and supplemental betaine. Betaine is supplemented in the range of 0.01% to 0.4%. Preferably, supplementation is in the range of 0.05% to 0.2% and more preferably, about 0.15% betaine is added.

The present invention is also directed to a method for supplementing the diets of domestic food animals with betaine in order to reduce mortality; to reduce carcass fat; and to improve carcass quality. The method involves supplementing standard basal diets with betaine; determining an optimum percentage of betaine supplementation; and using the optimum percentage of betaine to raise animals thereafter. The diets comprised of feedstuffs formulated using standard feed formulation tables and an optimum percentage of betaine are also encompassed by the present invention.

DETAILED DESCRIPTION OF THE INVENTION

A. Definitions

Figure 1:
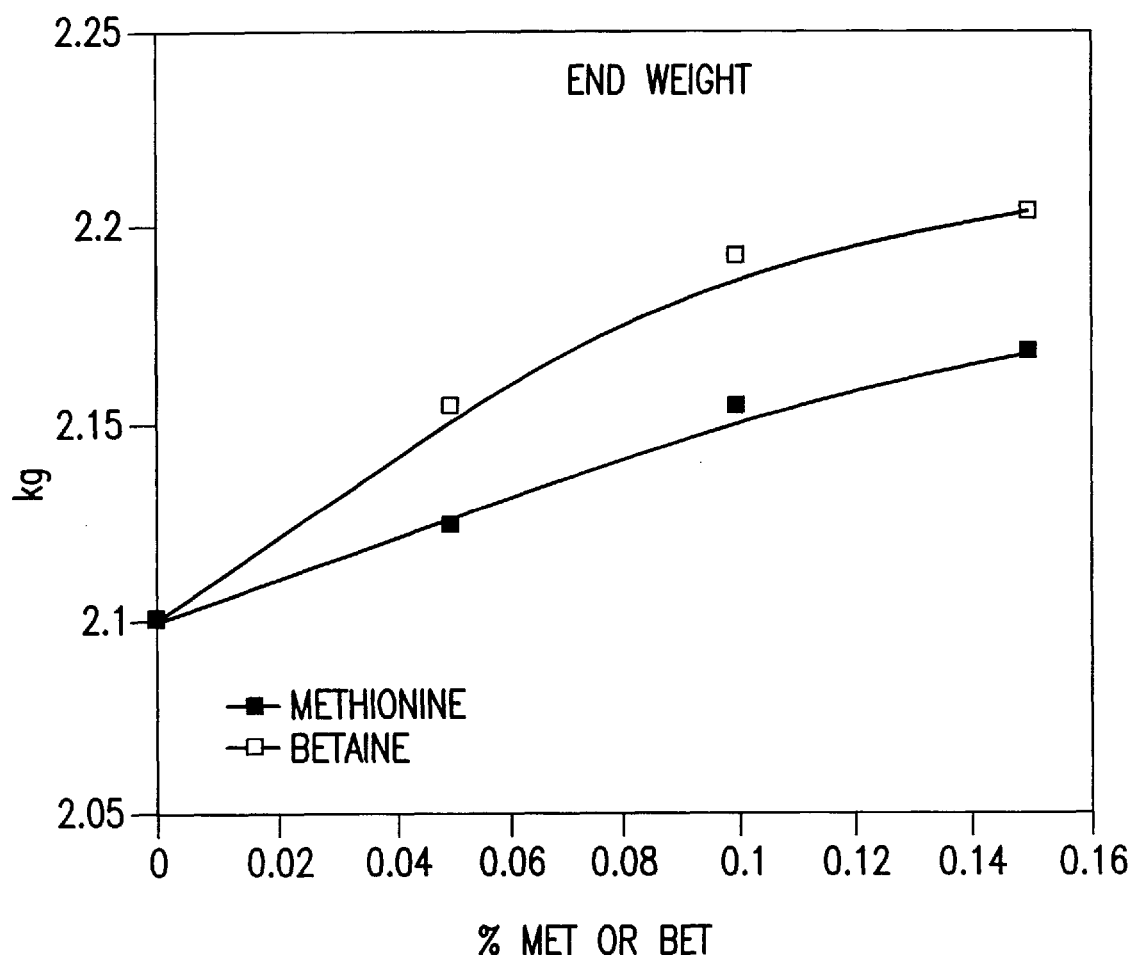
FIG. 1 shows the weight of chicks fed diets supplemented with either betaine (open squares) or methionine (darkened squares). The basal diet in this and all other experiments was adjusted to a concentration of 0.37% methionine for starter diets and 0.31% for grower/finisher diets before the additional methionine or betaine was added.

1. Starter diet: A "starter diet" is the diet fed to chickens during the first 21 days of life.
2. Grower diet: The term "grower diet" refers to the diet fed to chickens 21 to 40 days of age.
3. Finisher diet: The term "finisher diet" refers to the diet fed to chickens 40 to 49 days of age.
4. Betaine: "Betaine", also called "glycine betaine", is defined chemically as 1-Carboxy-N,N,N-trimethylmethaaminium hydroxide inner salt. Betaine is sold by Finnsugar Bioproducts under the tradename of "Betafin".
5. Feed conversion efficiency: "Feed conversion efficiency" is the ratio of the amount of feed consumed by an animal divided by the amount of weight gained by the animal. For example, a feed with an efficiency of 1.0 would mean that for every kilogram of feed consumed, the animal gained 1.0 kilogram.
6. Carcass composition or quality: "Carcass composition" and "carcass quality" refer to the relative size of the various edible parts or cuts of an animal and the ratio of fat to protein in the animal carcass. For example, a chicken carcass composed of a high percentage of breast meat and a low percentage of fat would have a desirable carcass composition and would be a high quality carcass.
7. Corn-soy feed: "Corn-soy feed" is feed mainly comprised of yellow corn, soybean meal and soy oil.
8. Significant: As used herein the term "significant" means statistically significant. Thus, a statement that "treated chicks had significantly reduced mortality relative to untreated chicks" means that $P<0.05$ using standard statistical analyses.
9. % LW: In experiments described herein, certain indicia of chick carcass quality are expressed in terms of % LW, an abbreviation for "percent lean weight". It is defined as the weight of a particular part of a chick carcass, e.g. breast meat or abdominal fat pad, divided by the total weight of the carcass multiplied by 100.
10. Mortality: Mortality is defined as the number of chicks within a treatment group that die during the course of an experiment. Typically mortality is expressed as a percentage and determined by dividing the number of chicks that die by the total number of chicks at the start of the experiment and then multiplying by 100.
11. Feedstuffs: "Feedstuffs" are defined as those commonly used ingredients such as yellow corn or soybean meal which are combined to formulate the diet of chicks.
12. Basal diet: "Basal diet" is defined as the diet to be fed to chicks prior to supplementation with either methionine or betaine.
13. Domestic Food Animal: For the purposes of the present invention, the term "domestic food animal" is defined as any domestic animal that is consumed as a source of protein in the diet of humans or other animals. Typical domestic animals include: bovine animals(e.g. cattle); ovine animals (e.g. sheep); swine (e.g. pigs); fowl (e.g. chickens and turkeys); rabbit and the like.
14. Optimum or Optimized: An optimum or optimized percentage of betaine is defined as the minimum percentage necessary to accomplish a defined objective. For example, the optimum percentage of betaine supplementation for reducing the mortality of domestic food animals would be the percentage which results in the lowest mortality. If 0.1% betaine and 0.15% betaine both resulted in chicks having the same mortality and this was the lowest mortality achievable with betaine supplementation, then the optimum percentage of betaine would be 0.1%.

B. Supplementation of Chick Diets with Betaine

The present invention is directed to a method of supplementing the diets of chicks using a combination of methionine and betaine. The method is more effective than methods supplementing diets with methionine alone at promoting growth, improving feed conversion efficiency and improving carcass quality.

The basal diet for broiler chicks is first formulated using any of a variety of routine feedstuffs such as corn, soy, wheat and barley (see *AFMA Feed Ingredient Guide*, published by the American Feed Manufacturer's Association, Arlington, Va., U.S.A.; H. Patrick et al., *Poultry: Feeds & Nutrition*, Second Edition, AVI Publishing Co. Inc., Westport, Conn., chapter 37, (1980)). All mixing of feedstuffs and preparation takes place using routine procedures well-known in the art (see e.g., H. Patrick et al., *Poultry: Feeds & Nutrition*, Second Edition, AVI Publishing Co. Inc., Westport, Conn., chapters 36–38 (1980); *Feed Manufacturing Technology*, H. Pfost and C. Swinehart eds., American Feed Manufacturer's Association Inc., Chicago, Ill., (1970)). The methionine content of the basal diet is determined using standard feedstuff analysis tables (see e.g., H. Patrick et al., *Poultry: Feeds & Nutrition*, Second Edition, AVI Publishing Co. Inc., Westport, Conn., pp. 438–449 (1980); H. Titus et al., *The Scientific Feeding of Chickens*, Fifth Edition, The Interstate Publishers, Danville, Ill., chapter 13 (1971)). For starter diets, supplemental methionine is added to a minimum final concentration of 0.37%. Other vitamins and minerals are added to concentrations determined by turning to various available references (see e.g., *Nutrient Requirements of Poultry*, National Research Council, National Academy of Sciences, Washington, D.C. (1977)). These references are well-known, and the data provided is generally accepted by those skilled in the art. Betaine is then added to the diet to a concentration of between 0.01% and 0.4% or, more preferably to a concentration of between 0.05% and 0.2%. In the experiment described in Example 1, betaine was added to diets to concentrations of 0.05%, 0.1%, and 0.15%.

Grower and finisher diets are prepared in a manner similar to starter diets except that the methionine content of the basal diet is adjusted to a minimum final concentration of 0.31%. Betaine is again added to a final concentration of between 0.01% and 0.4% (preferably between 0.05% and 0.2%). In the experiment described in Example 1, betaine was added to diets to concentrations of 0.05%, 0.1%, and 0.15%. In terms of final methionine and betaine concentrations, grower and finisher diets are identical.

The results shown in Example 1, Table IV demonstrate that chicks grown on diets supplemented with 0.05%, 0.10% or 0.15% betaine evidence a significant increase in body weight and a significant reduction in mortality compared to chicks grown on unsupplemented diets, i.e. the chicks in group T1. Chicks grown on diets supplemented with either 0.10% or 0.15% betaine show a significant improvement in feed conversion efficiency relative to chicks grown on unsupplemented diets. Compared to supplementation with methionine, diets supplemented with 0.05%, 0.10% or 0.15% betaine produced chicks with a significantly increased body weight. Diets supplemented with 0.15% betaine resulted in a significantly improved feed conversion efficiency and reduced mortality relative to diets supplemented with an equivalent amount of methionine. The decrease in mortality associated with betaine-supplemented diets is due to an ability of betaine to protect chicks against the harmful effects of coccidiosis infection. Thus betaine, either itself acts as an anticoccidial or it enhances the effect of other anticoccidials already present in diets.

The results in Table V demonstrate that chicks fed diets supplemented with 0.15 % betaine show a significantly improved body weight uniformity and a higher percentage of carcass breast meat than chicks fed unsupplemented diets, i.e. chicks in group T1. Chicks fed diets supplemented with either 0.10% or 0.15% betaine evidenced a significantly lower percentage of body fat than chicks fed unsupplemented diets. The results also show that betaine supplementation at a concentration of 0.15% produced chicks with a significantly improved carcass quality, in terms of a lower percentage of fat and an increased percentage of breast meat, than methionine supplementation at an equivalent amount. Overall, the results indicate the diets of chicks are most preferably supplemented with 0.15% betaine.

In other experiments, the concentration of methionine in basal diets was adjusted to a final concentration of 0.62% and additions of 0.02%, 0.06% and 0.20% betaine were made. Under these conditions, no significant effect of betaine addition was evidenced (data not shown). Therefore, the positive effects of betaine can be blocked at methionine concentrations substantially higher than those used in commercial broiler diets.

C. Supplementation of the Diets of Domestic Food Animals with Betaine

The methodology used to construct diets which reduce mortality by supplementing basal diets with betaine may be extended to other domestic food animals. This methodology and the resulting diets are encompassed by the present invention. A diet suitable for the particular domestic food animal being raised is formulated using standard feed tables. For example, a standard diet for cattle may be formulated using the information provided by the Merck Veterinary Manual, sixth edition, pages 1104–1132 (1986). Using the same source, standard diets can be prepared for rabbits (pages 1210–12110); sheep (1211–1221); swine (pages 1221–1230); horses (1169–1185); and poultry (pages 1188–1210). The standard diet is supplemented with from 0% to 0.4% betaine (by weight) and preferably with 0.1% to 0.2% betaine (by weight). The diet comprised of standard feedstuffs supplemented with an optimum percentage of betaine for reducing mortality, is encompassed by the present invention.

Diets comprised of standard feedstuffs supplemented with an optimum percentage of betaine for reducing carcass fat and for improving carcass quality are also encompassed by the present invention. Methods for determining carcass fat and carcass quality for different animals are well known in the art (Beck et al., U.S. Pat. No. 5,128,127; National Research Council, *Designing Foods, Animal Product Options in the Marketplace*, pages 242–278 (1988)). Again, a diet suitable for the particular domestic food animal being raised is formulated using standard feed tables such as those found in the Merck Veterinary Manual (cited above). The standard diet is supplemented with from 0% to 0.4% betaine (by weight) and preferably with 0.15% to 0.4% betaine (by weight).

A method for supplementing the diets of domestic food animals with betaine in order to reduce carcass fat comprises the steps of (a) formulating a diet for the domestic food animals using standard feed formulation tables; (b) dividing the domestic food animals into a minimum of three groups with a minimum of eight domestic food animals in each group; (c) feeding each group the diet of step (a) wherein the diet is supplemented with between zero and 0.4 percent betaine; (d) raising the domestic food animals for a conventional period of time; (e) measuring the carcass fat of each group of domestic food animals using standard techniques; (f) repeating the process of steps (a)–(e) at higher percentages of betaine until an optimum value for betaine supplementation is determined; and (g) supplementing the diets of all said domestic food animals with the optimum percentage of betaine determined in step (f).

A method for supplementing the diets of domestic food animals with betaine in order to improve carcass quality comprises the steps of (a) formulating a diet for the domestic food animals using standard feed formulation tables; (b) dividing the domestic food animals into a minimum of three groups with a minimum of eight domestic food animals in each group; (c) feeding each group the diet of step (a) wherein the diet is supplemented with between zero and 0.4 percent betaine; (d) raising the domestic food animals for a conventional period of time; (e) measuring the carcass quality of each group of domestic food animals using standard techniques; (f) repeating the process of steps (a)–(e) at higher percentages of betaine until an optimum value for betaine supplementation is determined; and (g) supplementing the diets of all said domestic food animals with the optimum percentage of betaine determined in step (f).

Having now described the invention in general terms, the same will be further described by reference to a specific example provided herein for the purpose of explanation only and not intended to be limiting unless otherwise specified.

EXAMPLE I

Combination of Betaine and Methionine as a Supplement for Chick Diets

In this example, chicks were grown for a total of 45 days. The grower diets (i.e. the diets used for chicks 21–40 days old) and finisher diets (i.e. the diets used for chicks 40–49 days old) were the same. For simplicity, these are referred to only as "grower diets". Formulations of starter and grower chicken diets prior to the addition of betaine were as follows:

TABLE I

| Ingredient | Starter | Grower |
| --- | --- | --- |
| Yellow corn | 60.85 | 65.82 |
| Soybean meal (48%) | 32.16 | 27.27 |
| Soy oil | 4.02 | 4.08 |

TABLE I-continued

| Ingredient | Starter | Grower |
|---|---|---|
| Salt | 9.21 | 0.25 |
| Defl. Phos. (32–18) | 1.71 | 1.47 |
| Limestone | 0.72 | 0.95 |
| Vitamin premix | 0.05 | 0.05 |
| Trace mineral premix | 0.05 | 0.05 |
| DL-methionine[1] | 0.03 | 0.00 |
| BioCox ® (30 g/t) | 0.10 | 0.10 |
| Bacitracin MD ® | 0.05 | 0.05 |
| Sum | 100.00 | 100.00 |

[1]Supplementation level according to our experience to reach the estimated specific requirement of methionine As shown in Table 2, the grower diet has a methionine content of 3.1 g/kg, with the sum of methionine and cysteine equal to 6.5 g/kg. Methionine was added to the starter diet to bring its level up to 3.7 g/kg, with the sum of methionine and cysteine equal to 7.3 g/kg. The calculated amount of various other nutrients contained in the diets at this stage is shown in Table II.

TABLE II

| Calculated analysis: | Starter | Grower |
|---|---|---|
| Crude Protein (%) | 21.00 | 19.00 |
| Total lysine (%) | 1.20 | 1.00 |
| Total methionine (%) | 0.37 | 0.31 |
| Total met + cys (%) | 0.73 | 0.65 |
| Total choline (%) | 0.142 | 0.145 |
| Total calcium (%) | 0.90 | 0.90 |
| Available phosphorous (%) | 0.45 | 0.40 |
| Dietary energy (MJ/kg) | 13.35 | 13.58 |

At this point both the grower diet and the starter diet were divided into seven equal fractions, designated as T1, T2... T7. Each fraction was further supplemented with either betaine or methionine in the amounts indicated in table III.

TABLE III

| | Starter Diet | | Grower Diet | |
|---|---|---|---|---|
| | Methionine | Betaine | Methionine | Betaine |
| T1 | 0 | 0 | 0 | 0 |
| T2 | 0.5 g/kg | 0 | 0.5 g/kg | 0 |
| T3 | 1.0 g/kg | 0 | 1.0 g/kg | 0 |
| T4 | 1.5 g/kg | 0 | 1.5 g/kg | 0 |
| T5 | 0 | 0.5 g/kg | 0 | 0.5 g/kg |
| T6 | 0 | 1.0 g/kg | 0 | 1.0 g/kg |
| T7 | 0 | 1.5 g/kg | 0 | 1.5 g/kg |

Each fraction was then fed ad libitum to 640 chickens kept in 8 pens. A complete record of all relevant parameters was maintained and is presented in tables IV and V.

TABLE IV

Days 1–45 DATA

| Treatment Number | Added Methionine (%) | Added Betaine (%) | Body Weight (1b) | Feed: Gain | Mortality (%) |
|---|---|---|---|---|---|
| T1 | 0.00 | 0.00 | 4.625 D | 1.862 C | 8.906 C |
| T2 | 0.05 | 0.00 | 4.678 CD | 1.849 BC | 7.500 BC |
| T3 | 0.10 | 0.00 | 4.744 BC | 1.842 BC | 3.906 AB |
| T4 | 0.15 | 0.00 | 4.777 AB | 1.839 BC | 6.719 BC |
| T5 | 0.00 | 0.05 | 4.746 BC | 1.846 BC | 4.063 AB |
| T6 | 0.00 | 0.10 | 4.831 AB | 1.831 AB | 5.156 AB |
| T7 | 0.00 | 0.15 | 4.854 A | 1.811 A | 1.875 A |

*ANOVA performed on measured parameters. Parameters marked with same letter are not significantly different at the 0.05 level.

TABLE V

Days 45 DATA (Processing Factors)   Trial 92–47

| Treatment Number | Added Methionine (%) | Added Betaine (%) | Body Weight Uniformity | Breast Meat (% LW) | Abdominal FAT PAD (% LW) |
|---|---|---|---|---|---|
| T1 | 0.00 | 0.00 | 12.82 BC | 12.97 AB | 2.78 D |
| T2 | 0.05 | 0.00 | 12.91 C | 12.66 A | 2.71 CD |
| T3 | 0.10 | 0.00 | 12.41 BC | 13.00 AB | 2.68 BCD |
| T4 | 0.15 | 0.00 | 12.16 AB | 13.48 BC | 2.55 BC |
| T5 | 0.00 | 0.05 | 12.96 C | 12.90 A | 2.69 BCD |
| T6 | 0.00 | 0.10 | 12.78 BC | 13.08 AB | 2.50 B |
| T7 | 0.00 | 0.15 | 11.58 A | 13.98 C | 2.25 A |

*ANOVA performed on measured parameters. Parameters marked with same letter are not significantly different at the 0.05 level.

Figure 2:
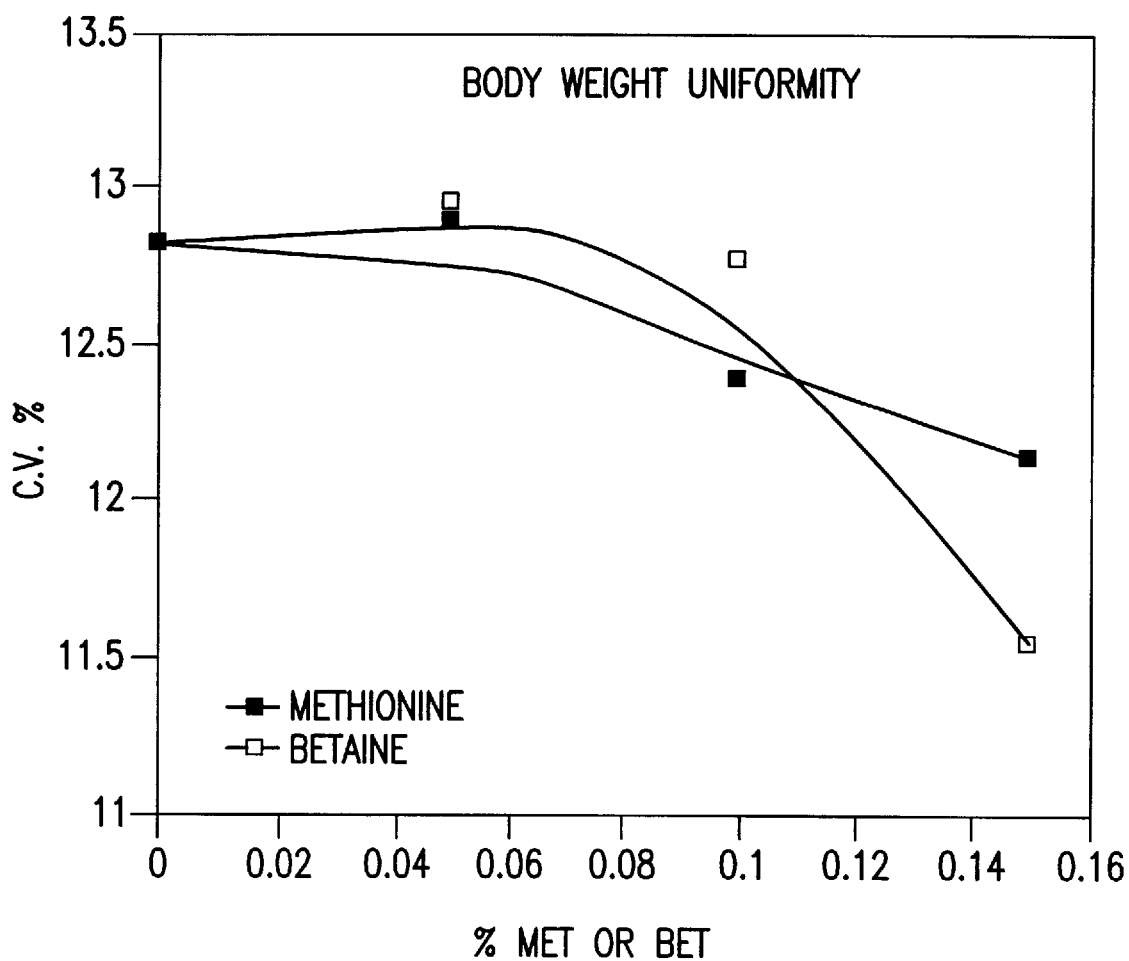
FIG. 2 shows the effect of supplementing the diets of chicks with betaine (open squares) or methionine (darkened squares) on body weight uniformity.
Figure 3:
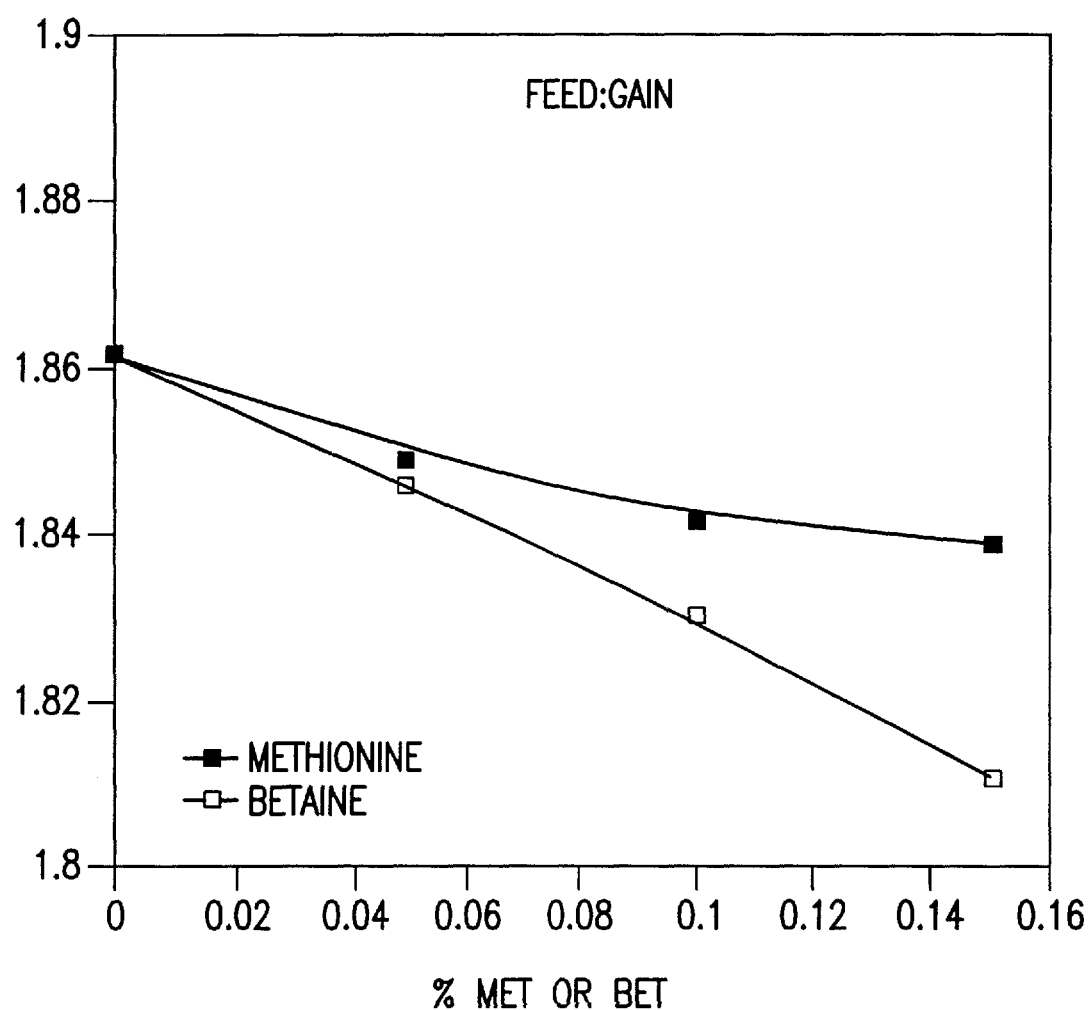
FIG. 3 shows the feed conversion efficiencies obtained from chicks fed diets supplemented with either betaine (open squares) or methionine (darkened squares).
Figure 4:
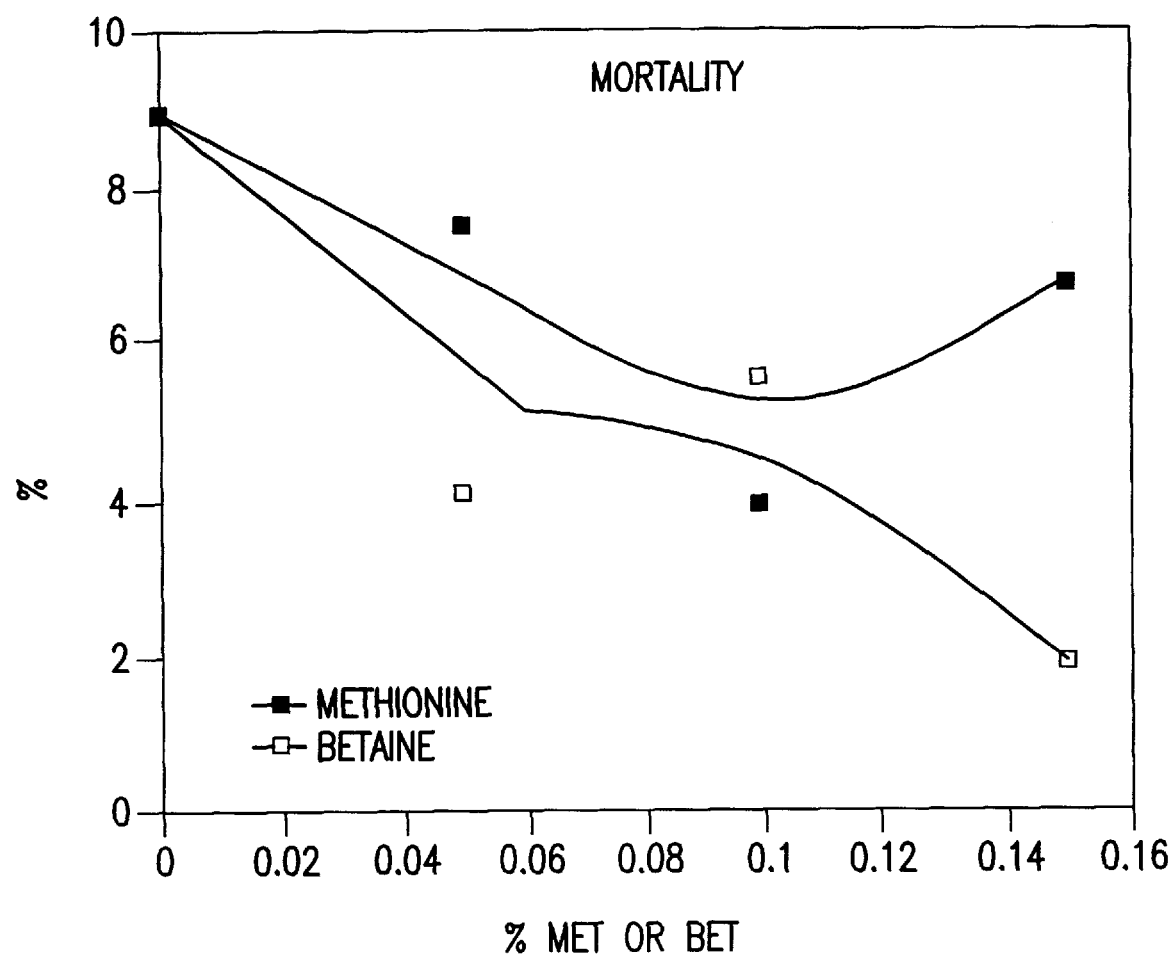
FIG. 4 shows the relationship between chick mortality (expressed as the percentage of chicks that died during the experiment) and supplementation of diets with either betaine (open squares) or methionine (darkened squares).
Figure 5:
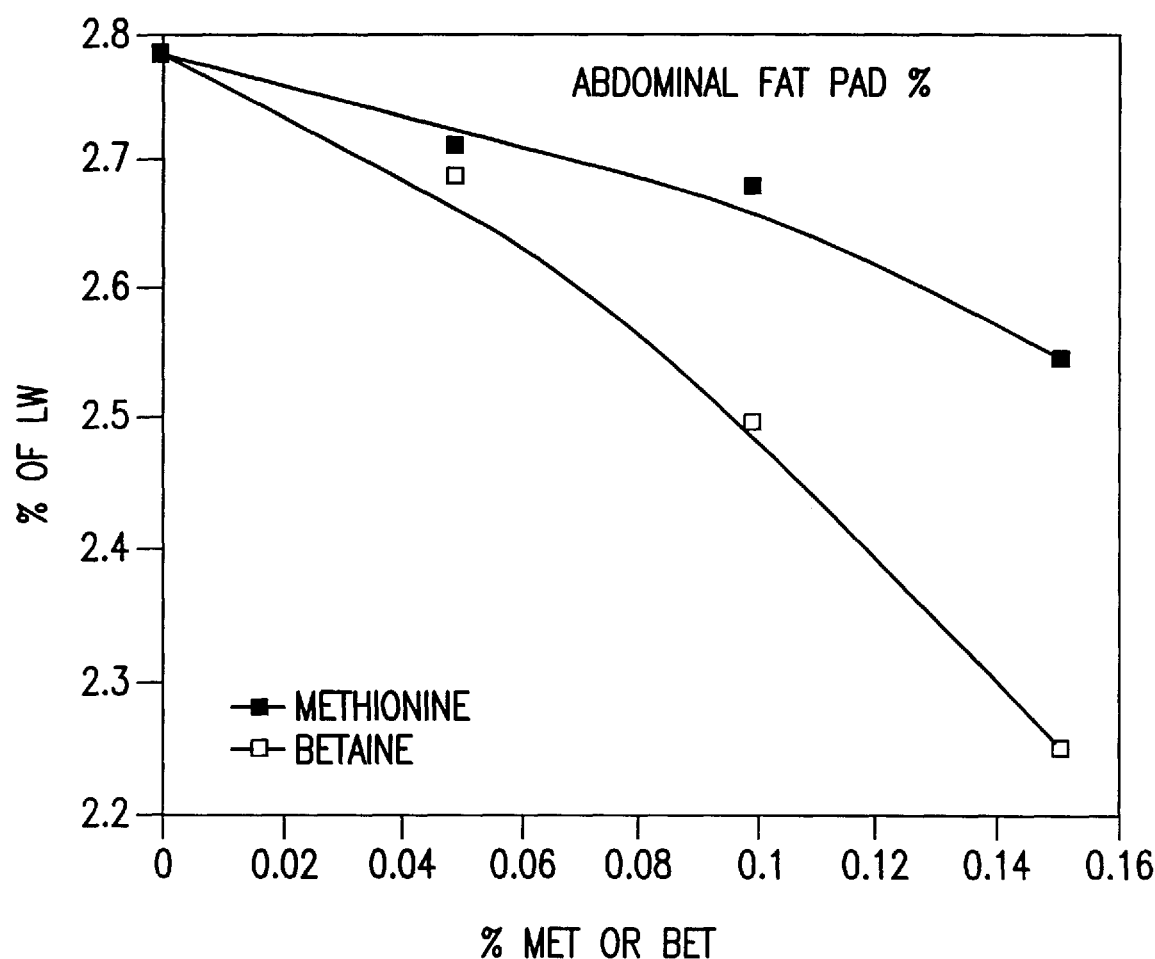
FIG. 5 shows the relationship between the weight of chick abdominal fat pads (expressed as a percentage of the lean weight of carcasses) and supplementation of diets with either betaine (open squares) or methionine (darkened squares).
Figure 6:
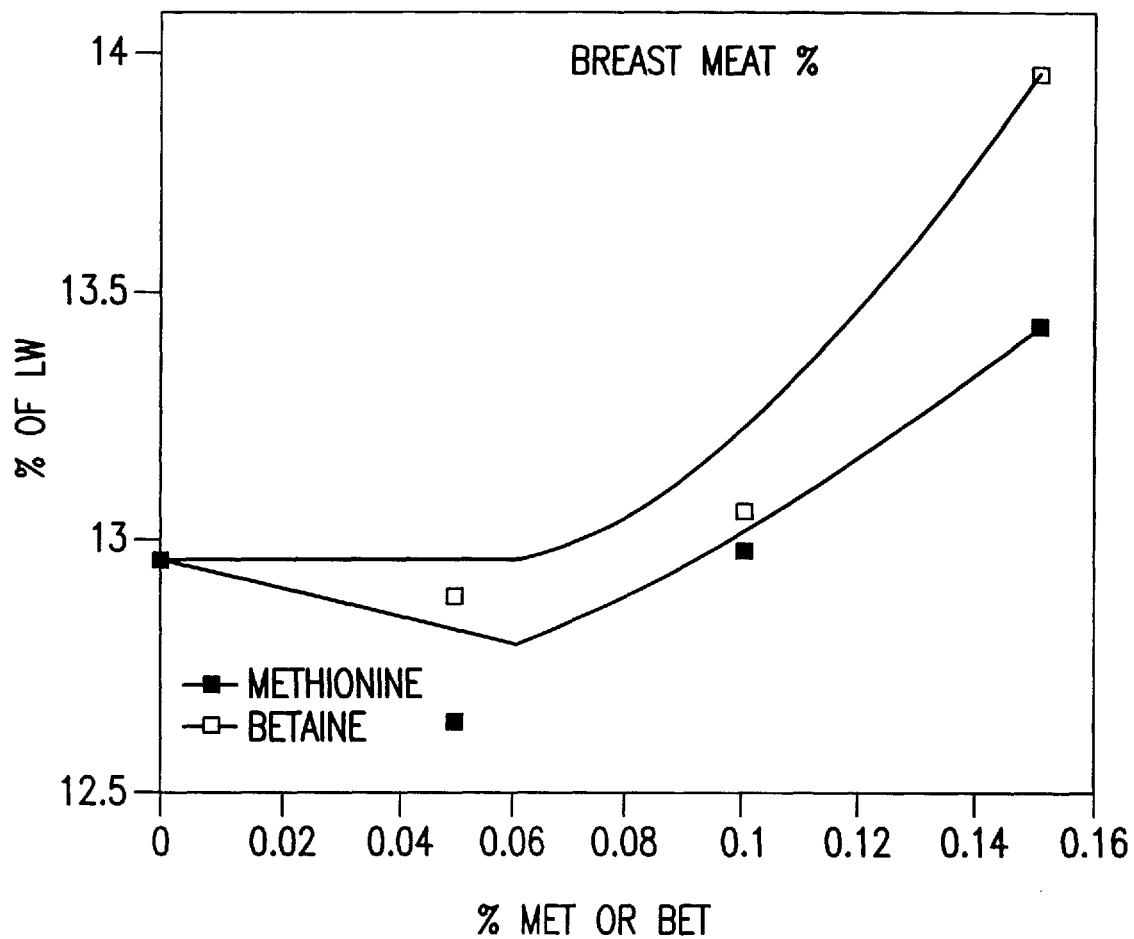
FIG. 6 shows the relationship between chick breast meat (expressed as a percentage of the lean weight of carcasses) and supplementation of diets with either betaine (open squares) or methionine (darkened squares).
Figure 7:
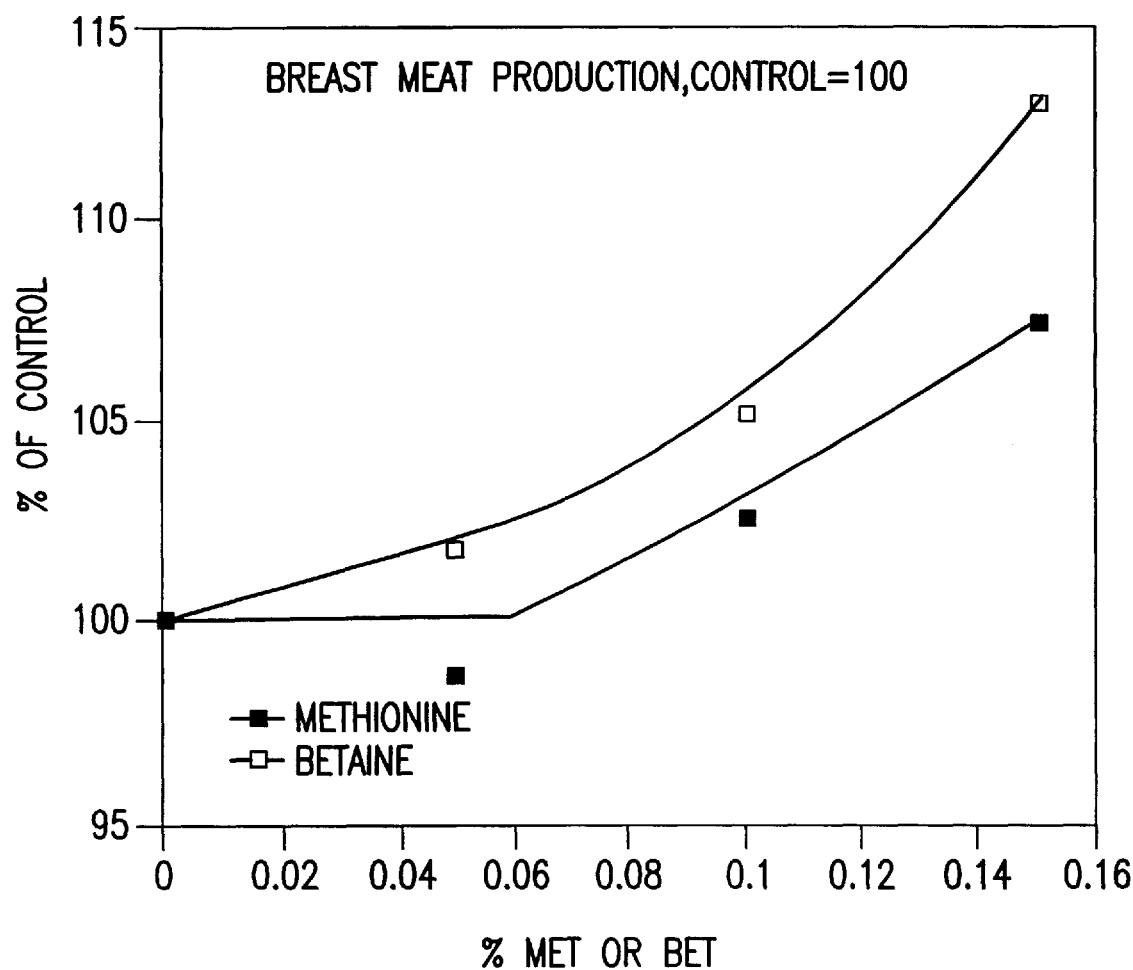
FIG. 7 shows the relative weight of breast meat in chicks grown on diets supplemented with either betaine (open squares) or methionine (darkened squares) compared with control chicks, grown on the same diets but without supplementation.

A comparison of the various measured parameters including growth, feed conversion efficiency, abdominal fat pad, and percentage breast meat was made between chickens fed a diet supplemented with betaine and methionine, and those fed a diet supplemented with just methionine. The results of this comparison are illustrated in FIGS. 1–7.

The data shows that supplementation with betaine and methionine is more potent than methionine alone in promoting an increase in growth, feed conversion efficiency, and carcass quality. Using a linear response model, betaine was estimated to be 2.3 times more effective at increasing weight gain and improving feed conversion efficiency than methionine. The results also indicate that the optimal level of betaine supplementation is 0.1%–0.2% (w/w) when the methionine level is restricted to 0.37% in starter diets and 0.31% in grower and finisher diets.

Although this invention has been described with particular reference to chickens, there is no scientific basis for excluding its application to other types of fowl such as duck or turkey or other types of domestic food animals. While the invention is described in detail in its preferred embodiments, it will be obvious to those skilled in the art that various changes and modifications may be made without departing from the spirit or scope of the invention. The appended claims are intended to cover all such modifications and changes.

What is claimed is:

1. A method of decreasing the percent carcass fat in a fowl, said method comprising feeding said fowl a diet containing at least 0.01% betaine and at least 0.31% methionine and a total concentration of betaine plus methionine of up to 0.71% of said feed, or wherein said diet contains at least 0.01% betaine and at least 0.37% methionine and a total concentration of betaine and methionine of up to 0.77% of said feed.

2. The method of claim 1, wherein said fowl is a chicken.

3. A method of increasing the percentage of carcass breast meat in a fowl, said method comprising feeding said fowl a diet containing at least 0.01% betaine and 0.31% methionine and a total concentration of betaine plus methionine of up to 0.71% of said feed, or wherein said diet contains at least 0.01% betaine and at least 0.37% methionine and a total concentration of betaine and methionine of up to 0.77% of said feed.

4. The method of claim 3, wherein said fowl is a chicken.

5. A method of increasing the feed conversion efficiency in a fowl, said method comprising feeding said fowl a diet containing at least 0.01% betaine and at least 0.31% methionine and a total concentration of betaine plus methionine of up to 0.71% of said feed, or wherein said diet contains at least 0.01% betaine and at least 0.37% methionine and a total concentration of betaine and methionine of up to 0.77% of said feed.

6. The method of claim 5, wherein said fowl is a chicken.

7. The method of any one of claims 1–6, wherein the amount of betaine added to the diet is between 0.05% and 0.2%.

8. The method of claim 7, wherein the amount of betaine added to the diet is 0.15%.

9. The method of any of claims 1–6, wherein a minimum of 50% of the diet is comprised of yellow corn and soybean meal.

10. The method of any one of claims 1–6, wherein said fowl is 0–21 days of age.

11. The method of claim 10, wherein the concentration of methionine is 0.37%.

12. The method of any one of claims 1–6, wherein said fowl is over 21 days of age.

13. A feed for fowl 0–21 days of age, said feed comprising at least 0.01% betaine and at least 0.37% methionine, wherein the total concentration of betaine plus methionine is up to 0.77% of said feed, wherein said betaine and said methionine are present in amounts that increase the feed conversion efficiency in fowl fed said feed, as compared to said feed conversion efficiency in fowl fed a feed containing an equivalent amount of methionine in place of the added betaine.

14. The feed of claim 13, wherein said fowl is a chicken.

15. A feed for fowl over 21 days of age, said feed comprising at least 0.01% betaine and at least 0.31% methionine, wherein the total concentration of betaine plus methionine is up to 0.71% of said feed, wherein said betaine and said methionine are present in amounts that increase the feed conversion efficiency in fowl fed said feed, as compared to said feed conversion efficiency in fowl fed a feed containing an equivalent amount of methionine in place of the added betaine.

16. The feed of claim 15, wherein said fowl is a chicken.

17. The feed of any one of claims 13–16, wherein the amount of said betaine is between 0.05% and 0.2%.

18. The feed of claim 17, wherein the amount of said betaine is 0.15%.

19. The feed of any one of claims 13–16, wherein a minimum of 50% of the diet is comprised of yellow corn and soybean meal.

20. A method of raising fowl, said method comprising feeding said fowl from 0–21 days of age a diet comprising at least 0.01% betaine and at least 0.37% methionine, wherein the total concentration of betaine plus methionine is up to 0.77%, and thereafter feeding said fowl a diet comprising at least 0.01% betaine and at least 0.31% methionine, wherein the total concentration of betaine plus methionine is up to 0.71%.

21. The method of claim 20, wherein said fowl is a chicken.

22. A method of decreasing the mortality rate in a group of fowl, said method comprising feeding said fowl a diet containing at least 0.01% betaine and at least 0.31% methionine and a total concentration of betaine plus methionine of up to 0.71% of said feed, or wherein said diet contains at least 0.01% betaine and at least 0.37% methionine and a total concentration of betaine and methionine of up to 0.77% of said feed.

23. The method of claim 22, wherein said fowl is a chicken.

24. The method of any one of claims 1, 3, 5, or 22, wherein the total concentration of betaine plus methionine is up to 0.51%.

25. The method of claim 20, wherein in said diet fed to said fowl from 0–21 days of age, the total concentration of betaine plus methionine is up to 0.57%, and wherein in said diet fed to said fowl thereafter, the total concentration of betaine plus methionine is up to 0.51%.

26. The method of any one of claims 1, 6, 22, or 23, wherein said diet contains at least 0.01% betaine and at least 0.31% methionine and a total concentration of betaine plus methionine of up to 0.71% of said feed.

27. The method of any one of claims 1, 6, 22, or 23, wherein said diet contains at least 0.01% betaine and at least 0.37% methionine and a total concentration of betaine and methionine of up to 0.77% of said feed.

* * * * *

UNITED STATES PATENT AND TRADEMARK OFFICE
CERTIFICATE OF CORRECTION

PATENT NO. : 5,773,052

DATED : June 30, 1998

INVENTORS : Virtanen *et al.*

It is certified that an error appears in the above-identified patent and that said Letters Patent is hereby corrected as shown below.

On the title page, item: [73] Assignee," delete "Cultor-Ltd," and insert therefor --Cultor Ltd,--.

In claim 1, line 5, please delete "feed" and insert therefor --diet--.

In claim 1, last line, please delete "feed" and insert therefor --diet--.

In claim 3, line 5, please delete "feed" and insert therefor --diet--.

In claim 3, last line, please delete "feed" and insert therefor --diet--.

In claim 5, line 5, please delete "feed" and insert therefor --diet--.

In claim 5, last line, please delete "feed" and insert therefor --diet--.

In claim 22, line 5, please delete "feed" and insert therefor --diet--.

In claim 22, last line, please delete "feed" and insert therefor --diet--.

UNITED STATES PATENT AND TRADEMARK OFFICE
CERTIFICATE OF CORRECTION

PATENT NO. : 5,773,052

DATED : June 30, 1998

INVENTORS : Virtanen *et al.*

It is certified that an error appears in the above-identified patent and that said Letters Patent is hereby corrected as shown below.

In claim 26, line 1, delete "1, 6," and insert therefor --1-6,--.

In claim 26, last line, please delete "feed" and insert therefor --diet--.

In claim 27, line 1, delete "1, 6," and insert therefor --1-6,--.

In claim 27, last line, please delete "feed" and insert therefor --diet--.

Signed and Sealed this

Twenty-third Day of February, 1999

Attest:

Q. TODD DICKINSON

Attesting Officer     Acting Commissioner of Patents and Trademarks